US00PP21185P3

(12) United States Plant Patent
Hall et al.

(10) Patent No.: US PP21,185 P3
(45) Date of Patent: Aug. 10, 2010

(54) RASPBERRY PLANT NAMED 'WAKEFIELD'

(50) Latin Name: ***Rubus idaeus* L.**
Varietal Denomination: Wakefield

(75) Inventors: Harvey K. Hall, Motueka (NZ); Joseph Stephens, Auckland (NZ)

(73) Assignee: The New Zealand Institute for Plant and Food Research Limited, Auckland (NZ)

( * ) Notice: Subject to any disclaimer, the term of this patent is extended or adjusted under 35 U.S.C. 154(b) by 0 days.

(21) Appl. No.: 12/317,702

(22) Filed: Dec. 26, 2008

(65) Prior Publication Data

US 2010/0170019 P1 Jul. 1, 2010

(51) Int. Cl.
*A01H 5/00* (2006.01)

(52) U.S. Cl. ..... Plt./204

(58) Field of Classification Search ..... Plt./204
See application file for complete search history.

*Primary Examiner*—Annette H Para
(74) *Attorney, Agent, or Firm*—Greenlee Winner and Sullivan PC

(57) ABSTRACT

A new and distinct floricane fruiting red raspberry, *Rubus idaeus* L., variety is described. The variety results from selection among a population of seedlings derived from controlled pollination crossing of the raspberry varieties known as 'Lewis' (not patented) and selection 86105M57 (not patented). The new variety is distinguished from others by the semi crown-forming nature of the plant which tends to produce fewer thicker canes that tend to branch and are very vigorous. The variety is further distinguished by having fruit that ripen on long laterals, release from the receptacle very easily, are dark in color, have large drupelets, and are very firm. In addition, the plant has displayed some field resistance to root rot caused by *Phytophthora fragariae* var. *rubi* and appears to be tolerant to infection of Raspberry Bushy Dwarf Virus (RBDV). Fruit of the new variety appears very suitable for the process fruit market.

5 Drawing Sheets

Genus and species of plant claimed: *Rubus idaeus* L.
Variety denomination: Wakefield

BACKGROUND TO THE INVENTION

The new variety of red raspberry, *Rubus idaeus* L., was created in the course of a planned breeding program carried at Riwaka Nelson, New Zealand. The parents used to make the cross were the unpatented selection ORUS 576-47 (since named 'Lewis') (seed parent) from Oregon and the unreleased, unpatented selection 86105M57 (pollen parent) from Riwaka, New Zealand.

The controlled cross performed to produce 'Wakefield' was carried out in a greenhouse in 1990 and resulting seed was germinated and grown at Riwaka, Nelson, New Zealand. A total of 115 seedlings were planted on land at Riwaka in 1991. The original plant of the new variety was selected and given the breeders code 90352EK-6 (and subsequently recoded as HR40 at the advanced selection stage) during the 1993-94 summer (Southern Hemisphere).

SUMMARY OF THE INVENTION

Key characteristics of 'Wakefield' are:

(a) A plant that is partially crown-forming and produces primocanes that are very vigorous, thick and tend to branch.

(b) The ability to form medium sized, very firm fruit, that are very easy to pick, dark red in color, ovate-round in shape (FIG. 2) with very good flavor and high soluble solids concentration. The fruit have a distinctive orange-colored receptacle and the combination of large drupelet size and low drupelet numbers per fruit are distinguishing features of the new variety.

(c) Production of high fruit yields; fruit produced on long fruiting laterals (FIG. 2) and ripening moderately late in the season.

The new variety was first asexually propagated at Riwaka, Nelson, New Zealand in 1994, being reproduced by vegetative cuttings arising from root cuttings. The resulting plants propagated true to type, demonstrating that the characteristics of the new variety are stable and are transmitted without change through succeeding generations. Since 2005, 'Wakefield' has been asexually propagated in vitro via tissue culture methods. The variety has propagated true to type via these means at Riwaka, Nelson, New Zealand.

The new variety was tested and evaluated during the years 1996 to 1998 at Riwaka Nelson Region, New Zealand (41.10° S, 172.97° E) and during years 2005 to 2008 in test plots in Lynden, Washington State, United States of America (USA) (48.95° N, 122.44° W).

When compared to the seed parent 'Lewis' the new variety was found to have fruit that were smaller, darker and firmer. Also the plant exhibited a semi-crown forming growth habit which is unusual in red raspberry. 'Wakefield' plants were also found to be significantly less susceptible to RBDV than 'Lewis' plants.

When compared to selection 86105M57 'Wakefield' was found to have fruit that were significantly firmer and borne on longer laterals. In addition plants of 'Wakefield' have significantly more spines on canes than 86105M57, which is spineless.

BRIEF DESCRIPTION OF PHOTOGRAPHS

DETAILED DESCRIPTION

Horticultural terminology is used in accordance with UPOV guidelines for raspberry. All dimensions in millimeters, weights in grams (unless otherwise stated). Where a color reference is given these refer to The R.H.S. Colour Chart, The Royal Horticultural Society, London. 4$^{th}$ Edition, 2001. The specimens described were grown in Lynden, Wash. State, USA.

Environmental data for the Lynden, Wash., USA growing area demonstrates conditions in spring and early summer (equating to the harvest period for the variety) as follows:

- Spring (April/May); mean daily temperature in the range 10-11° C. (mean daily minimum 5.5° C., mean daily maximum 15.5° C.).
- Early summer (June/July); mean daily temperature 16° C. (mean daily minimum 10° C., mean daily maximum 21.5° C.).

In winter temperatures below 0° C. are common, the daily mean for December/January is 2.5° C. with the lowest temperature unlikely to be colder than - 13° C. Average annual rainfall is approximately 1500 mm.

Figure 3:
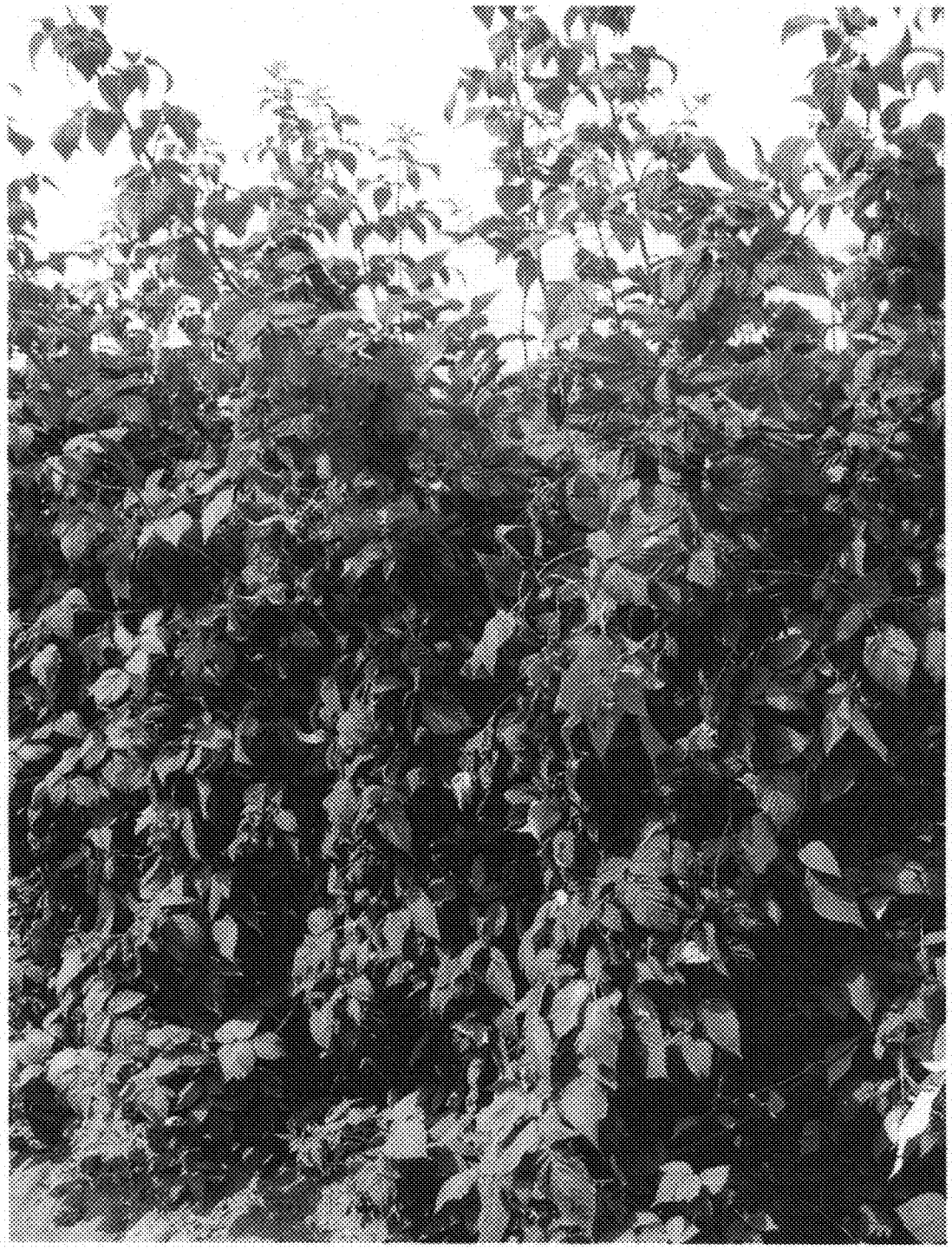
FIG. 3 shows a mature bush of the new variety 'Wakefield' view shows fruit and primocanes.
Figure 4:
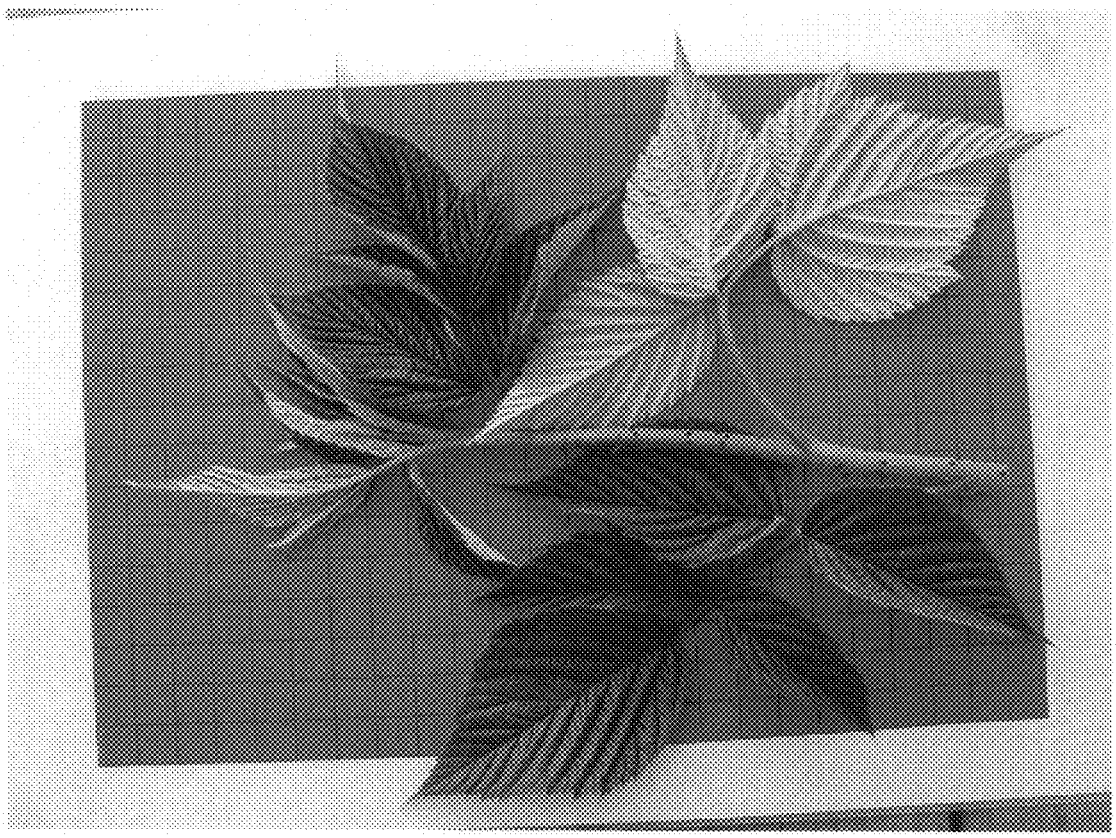
FIG. 4 shows the tip of the primocane of a plant of 'Wakefield'.
Figure 5:
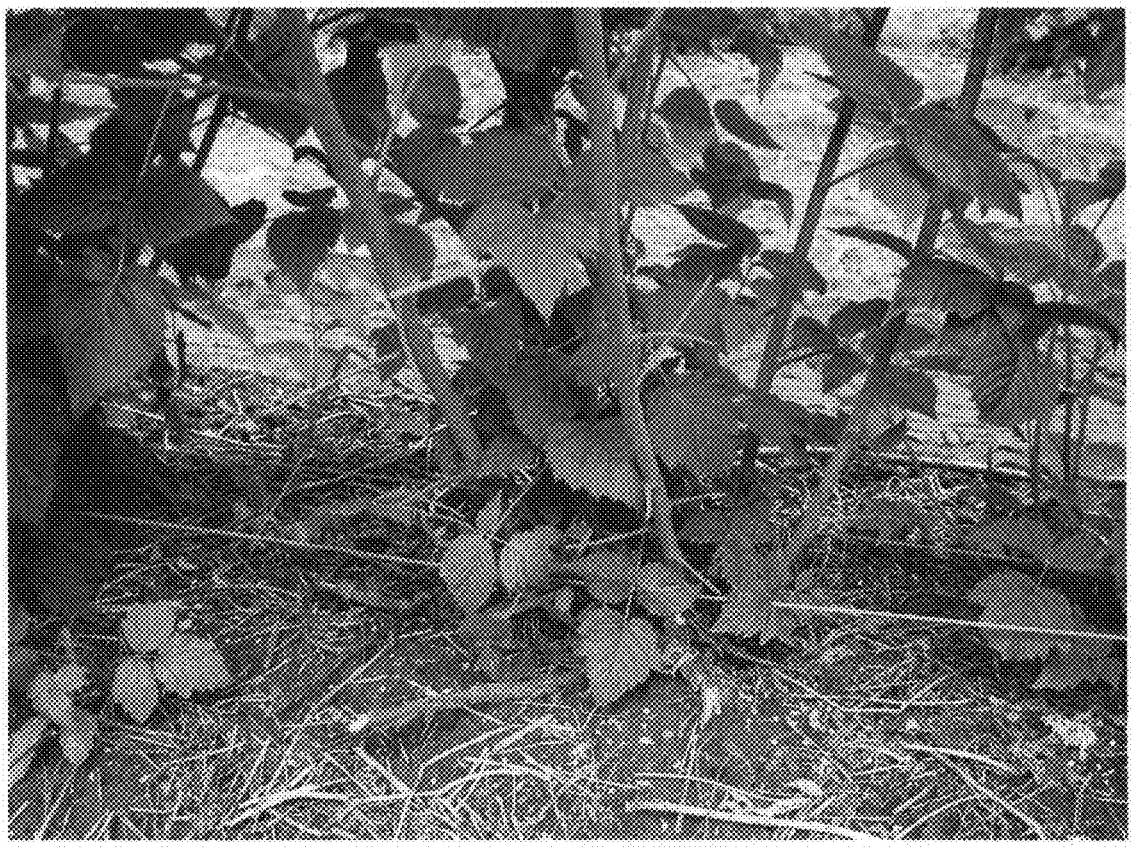
FIG. 5 shows the distinctive semi-crown forming nature of primocanes of the plant of the new variety 'Wakefield'.

Plant and foliage: Plants exhibit a very strong and medium upright growth habit (FIG. 3). Mature plant height is commonly in the range 2500 to 3000 mm, although this may vary with the growing conditions. Strong vigor is exhibited and internode length is typically long and in the range 120-130 mm. Plants have a moderate to low number of young shoots (typically 4-14 per plant) that tend to come from a centre crown and do not spread. Spines (prickles/thorns) are in general sparse, with the greatest density of spines near the base of canes, very few in the middle cane section and moderate numbers near the top of mature canes. Spines are typically approximately <1 mm long but may be denser and longer on juvenile canes. Plants have been observed to be less spiny compared with some other commercial varieties, for instance, 'Meeker' (not patented). Spine color is very dark (near purple N77A) which distinguishes the plant of the new variety from some commercially grown cultivars such as 'Meeker' and 'Willamette'. Canes are pubescent indicating the presence of gene H. Canes typically show light grey-brown coloration (near Grey-brown 199D in areas where the bark is intact and near Grey- brown N199B in areas where it has peeled) in winter. During the growing season generally the color on the canes is near Yellow-green N144B and Yellow-green 144A and there is little anthocyanin evident on the sun-exposed side of the cane. Young shoots are erect and are near Yellow-green 144A in color. The leaves are compound, moderately strongly crinkled, flat and moderately dull, with strong silver coloration on the leaf underside. (FIG. 4). The number of primocane leaflets per internode is predominantly five. The base of the terminal leaflet is concave in shape and typically averages 80-90 mm in diameter and 100-110 mm in length. The coloration of the upper surface of the leaf is green (near Yellow-green 146A on young foliage and near Green 137A on older foliage), the under side being markedly lighter in coloration (near Greyed-green 188B). 'Wakefield' foliage is typically darker in color than some commercially grown cultivars such as 'Meeker'. While the leaves do not have distinguished marginal or vein coloration, the venation has noticeable rises and falls. The leaf petiole typically ranges approximately 10-110 mm in length and averages 2.5 mm in diameter. It is near Yellow-green 144B in color. The fruit is borne on the previous year's growth. The fruiting laterals are very long in length, commonly measuring 800-1000 mm, are weakly ascending and horizontal at the start of the season and droop considerably as fruit ripens.

Inflorescence: White flowers are borne on short slender pedicels that have spines (thorns/prickles) that are sparse. Approximately half of the pedicels have no spines and the other half commonly have 1-2 spines per pedicel. At HortResearch Nelson, New Zealand the date bud burst commences is approximately 25 September, with fifty percent of buds burst by mid October. The time of bloom is late season for a summer-fruiting raspberry, with peak flowering late November. In the Pacific North West, USA, bud burst typically commences early-mid March with 50% buds burst by the end of March. Time of beginning of bloom is typically mid-late May and typically peaking mid June. Flowers are numerous and borne on a paniculate inflorescence. Typically there are five petals, elongated ovate in shape with a rounded apex and flat base. The petals average approximately 7.5-8.5 mm in length and 4.3 mm in width. They are typically smooth in texture, have a smooth margin and are near White 155B in color. The pedicel length averages approximately 20-25 mm long. However, the more basal the pedicel the longer it commonly becomes with pedicel lengths up to about 50 mm being observed. The pedicel averages approximately 1.0 mm in diameter and is near Yellow-green 146C in color and has weak anthocyanin coloration on the sun-exposed side. A typical king flower diameter is approximately 30 mm (from sepal tip to sepal tip i.e. the widest part of the flower). The flowers are predominantly borne singly or in pairs, although sometimes in clusters of three or more. Terminal branch flower clusters frequently consist of two flowers and basal flower clusters may number three to five. Un-opened flowers are characteristically long and narrow and slender when closed compared to other varieties. The flowers have no discernible fragrance. The nature of the growth of the sepals, is also a characteristic of the new variety. Initially the sepals open fully to expose the bloom and then several weeks later may partially close again around the immature green fruit before opening again prior to fruit ripening. Five sepals are present. These are green in coloration (near Grey-green 194B on the bottom and near Yellow-green 146D on top) and measure approximately on average 13 mm in length from base to tip. The reproductive organs are typical for flowers of *Rubus idaeus* L.; the stigmas average approximately 65 in number and are near Yellow-green 145C in color; there are approximately 75-80 stamens the filaments of which are near White 155C in color and average 3.8 mm in length. Anthers are brown and (depending on maturity) near Brown 200B in color.

Harvest: Fruit commences ripening in mid-late December in New Zealand: The typical start date for picking the new variety is 18 December. Fifty percent of the harvest is typically completed by 5 January, and the main harvest period is complete by mid-late January (approximately 23 January). 'Wakefield' is very suitable for harvest by machine due to the extreme ease with which fruit dislodges from the receptacle. In machine harvest trials in the Pacific North West 'Wakefield' fruit were removed very cleanly from the plant by the machine with very few green fruit knocked off with ripe fruit. Fruit is particularly firm and well suited to individually quick frozen (IQF) operations. The dark red color of the fruit means it is also suitable for other types of processing markets.

Figure 1:
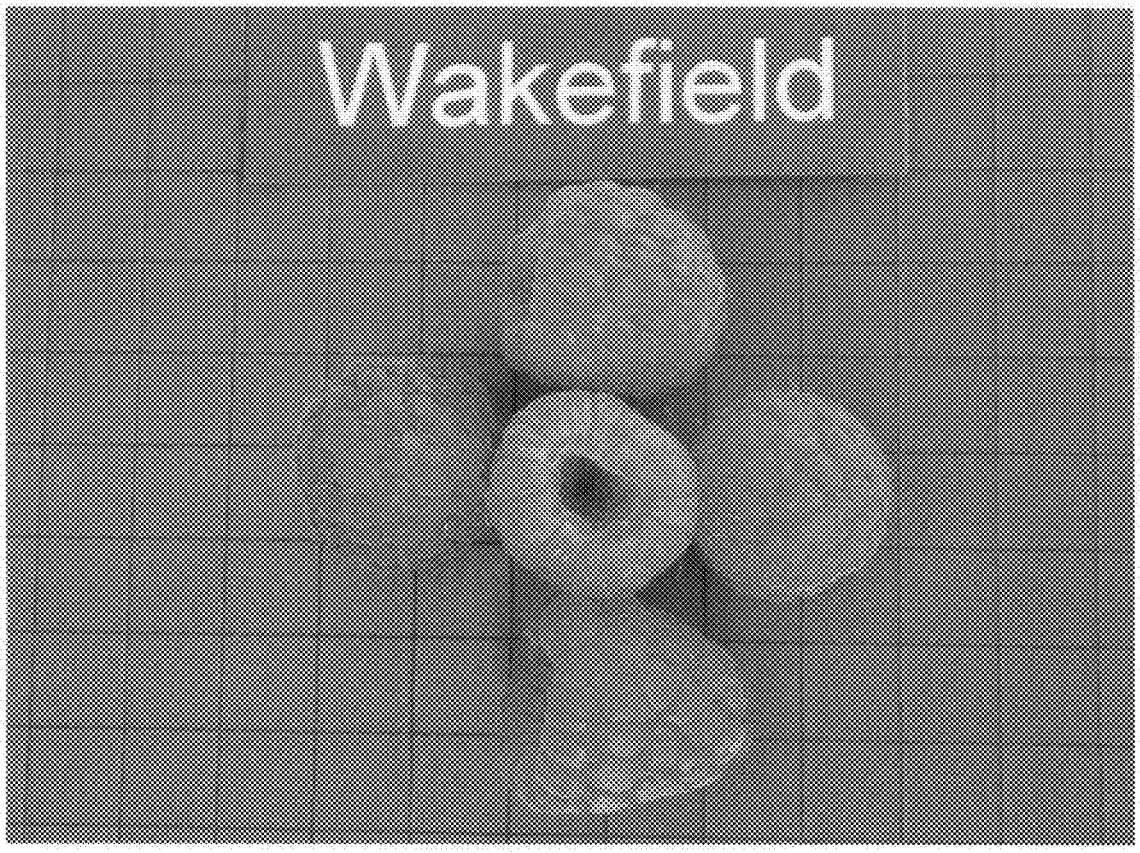
FIG. 1 shows fruit of the new variety 'Wakefield' on a 1 cm grid.
Figure 2:
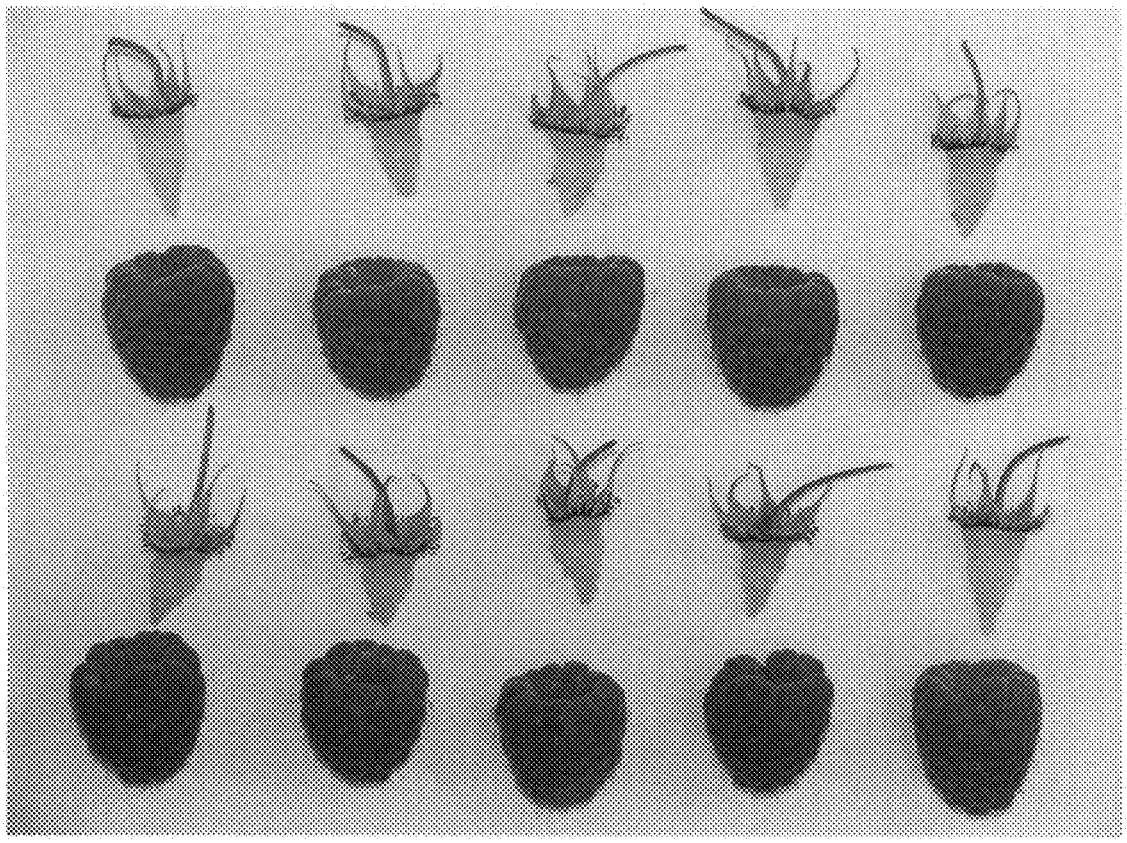
FIG. 2 shows fruit of the new variety 'Wakefield'; view shows the side profile of the berry and the distinctive orange receptacle.

Fruit: Fruit is produced on previous year's cane in summer. Berry size is medium. The average berry weight is approximately 4.0g; individual fruit ranging between 3-5g in weight. Fruit shape is ovate-round; on the basis of fruit length to width ratio, fruit is slightly longer than broad (FIG. 1). On average berries are typically 21.5 mm long and 20.5 mm wide at the widest point. Fruit color is medium-dark red; external color near Red-purple 59A and Purple N77; internal color near Red 53A. Fruit color of 'Wakefield' fruit has been observed to be similar or slightly darker than the commercial red raspberry variety, 'Meeker' (not patented), and lighter than 'Willamette'. The fruit skin of 'Wakefield' fruit shows medium dull glossiness as a result of hairs being present. Fruit drupelet size has been observed to be very large (typically 4.8 mm in diameter) compared with drupelet size of fruit of many other commercial red raspberry cultivars such as 'Meeker' (not patented) and 'Willamette'. Drupelet numbers are low for red raspberry, typically averaging 65 per fruit. Large drupelet size and low drupelet numbers are distinguishing features of the fruit of the new variety. The berries are very firm and of very good raspberry flavor. Soluble solids concentration is high (typically 10-12° Brix). The fruit receptacle is orange in colour (FIG. 2) which differentiates it from other commercial red raspberry cultivars such as 'Meeker' and 'Willamette'. The seeds average 2.7 mm long and 1.5 mm wide, and are near Red 36A in color when dry. Seed numbers per fruit average 65 and weigh on average 0.137 g per fruit (or average 2.1 mg individually). Fruit yields of 'Wakefield' are high. In trials in the Pacific North West machine harvested yields are typically 5-6t/ha equivalent.

Pest and disease resistance: The plant does seem to be susceptible to yellow rust (*Phragmidium rubi-idaei*). Since the selection of this clone in 1993-94 numerous tests for RBDV have been carried out on 'Wakefield' in New Zealand using enzyme-linked immunosorbent assay (ELISA). RBDV has been detected in trial plots of Wakefield' in New Zealand, however, infection was low in ten-year old plants and no obvious symptoms were observed in infected plants. In the Pacific North West 'Wakefield' has not tested positive for RBDV despite high infection pressure and multiple testing. From this we suggest that 'Wakefield' has some tolerance to the strains of RBDV found in New Zealand and the USA. Resistance to aphids is unknown. Initial results from in field testing show 'Wakefield' appears to have some field resistance to root rot caused by *Phytophthora fragariae* var. *rubi*.

Geographical adaptation: Observations indicate that the variety is well-suited to production in regions that offer a medium-high amount of winter chill, for example, 'Wakefield' performs well in USDA Plant Hardiness zones 8-10 (published as the 2003 US National Arboretum "Web Version" of the USDA Plant Hardiness Zone Map USDA Miscellaneous Publication No. 1475, Issued January 1990). 'Wakefield' also performs well in the cool temperate region of Nelson, New Zealand under standard management practices for commercial raspberry production.

We claim:

1. A new and distinct raspberry plant substantially as herein illustrated and described.

* * * * *